United States Patent [19]

Rapolthy

[11] 4,124,476
[45] Nov. 7, 1978

[54] ELECTROLYTIC CELL FOR THE PRODUCTION OF ALUMINIUM

[76] Inventor: Egon Rapolthy, Winterthurerstr. 152, Zürich, Switzerland, CH-8057

[21] Appl. No.: 805,906

[22] Filed: Jun. 13, 1977

[30] Foreign Application Priority Data

Jun. 16, 1976 [CH] Switzerland ............... 7718/76

[51] Int. Cl.² .................. C25C 3/08; C25C 3/06
[52] U.S. Cl. .................... 204/243 R; 204/67
[58] Field of Search ............ 204/243 R–247, 204/67

[56] References Cited

U.S. PATENT DOCUMENTS

| | | | |
|---|---|---|---|
| 2,991,235 | 7/1961 | Ravier | 204/243 R X |
| 3,494,851 | 2/1970 | Cauvin, Jr. | 204/243 R |
| 3,580,835 | 5/1971 | Peterson | 204/243 R |
| 3,764,509 | 10/1973 | Etzel et al. | 204/243 R |

Primary Examiner—John H. Mack
Assistant Examiner—D. R. Valentine

[57] ABSTRACT

The amount of bulging and cracking in the carbon floor of an electrolytic reduction cell for the production of aluminium is reduced by the provision of a recess in the steel container which accommodates the carbon floor as it expands. The recess is filled with a first material which is easily compressible and a second material which deforms only at a relatively higher load and transmits the expansion forces to the steel container without producing any permanent deformation thereof.

11 Claims, 8 Drawing Figures

ELECTROLYTIC CELL FOR THE PRODUCTION OF ALUMINIUM

BACKGROUND OF THE INVENTION

In the production of aluminum by the electrolysis of aluminum oxide ($Al_2O_3$), the aluminum oxide is dissolved in a fluoride melt consisting mainly of cryolite ($Na_3AlF_6$). The aluminum, which separates out at the cathode, collects below the fluoride melt on the floor of the cell, and the surface of the liquid aluminum forms the cathode of the cell. Anodes, which are made of amorphous carbon in conventional processes, are inserted into the melt from above. As a result of the electrolytic decomposition of the aluminum oxide, oxygen forms at the anodes and combines with the carbon of the anodes to produce CO and $CO_2$. The temperature range in which the electrolytic reaction takes place is approximately 940° C to 975° C.

Figure 1:
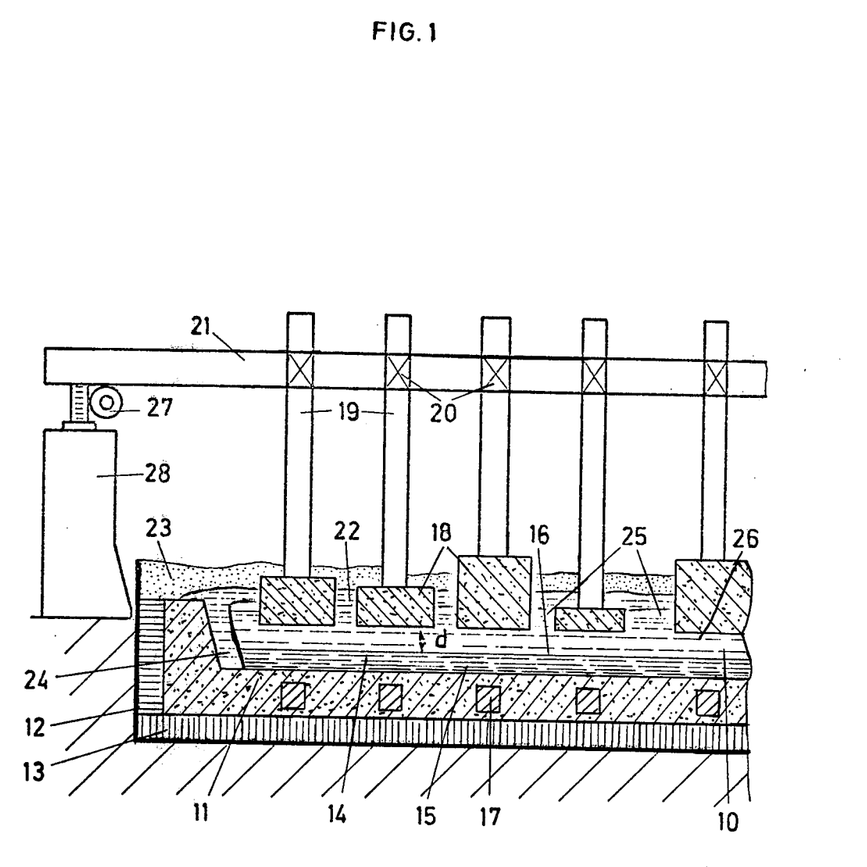
FIG. 1 shows the general arrangement of a cell of the prior art.

The well known principles of the prior art governing a conventional aluminum electrolytic cell, using prebaked carbon anodes, are illustrated in FIG. 1 of the accompanying drawings, which shows a vertical section along a longitudinal direction through a part of the cell. The fluoride melt 10, i.e. the electrolyte, is held in a steel container 12, which is lined with a thermally-insulating, refractory material 13 and with carbon 11. The aluminum 14 separated out at the cathode is lying on an upper surface 15 of the carbon floor of the cell. The cathode is formed by the surface 16 of the liquid aluminum. Within the carbon floor, and disposed in a direction transverse to the longitudinal direction of the cell, are iron cathode bars 17, which conduct direct current from the carbon lining 11 out of the cell. Anodes 18 made of amorphous carbon are inserted into the fluoride melt 10 from above and supply the electrolyte with direct current. The anodes 18 are connected via conductor rods 19 to the anode bus bar 21, to which the rods 19 are securely fixed by means of clamps 20. The electric current flows from the cathode bars 17 of one cell, through a busbar which is not illustrated here, to the bus bar 21 of the next cell connected in a series. The current flows from the bus bar 21, through the conductor rods 19, the anodes 18, the electrolyte 10, the liquid aluminum 14, and the carbon lining 11 to the cathode bars 17. The electrolyte 10 is covered by a crust 22 of solidified electrolyte, on top of which there is disposed a layer 23 of aluminum oxide. While the cell is in operation spaces 25 are formed between the electrolyte 10 and the crust 22. A crust of solidified electrolyte, i.e. a lateral ledge 24, also forms at the side wall of the carbon lining 11. This lateral ledge 24 determines the horizontal surface area of the bath of liquid aluminum 14 and of the electrolyte 10.

The distance D between the bottom 26 of the anode and the surface 16 of the aluminum, called alternatively the interpolar distance, can be changed by raising or lowering the bus bar 21 by means of jacks 27, which are mounted on columns 28. On operating the jacks 27, all the anodes are raised or lowered at the same time. The anodes can also be set individually at any chosen height by means of the clamps 20 disposed on the bus bar. bar 21.

Oxygen, which is released during electrolysis, reacts with the anodes, with the result that they are consumed at the bottom of the cell at the rate of approximately 1.5 to 2 cm per day, the amount depending on the type of cell. The cell is designed so that, at the same time, the surface of the liquid aluminum in the cell rises by 1.5 to 2 cm per day. After an anode has been consumed in this manner, it is replaced by a new anode. In practice, a cell is operated in such a way that after only a few days, the anodes are consumed in varying degrees, with the result that the anodes have to be replaced individually over a period of several weeks. This results, as is shown in FIG. 1, that anodes at different stages of their respective lifetimes are in operation in any one cell.

In the course of electrolysis the concentration of aluminum oxide in the melt 10 falls. When the concentration of aluminum oxide is as low as 1 - 2 %, an anode effect occurs, i.e. a sudden increase in voltage, from a normal 4 to 4.5 V, to 30 V and higher, is observed. Then the crust must be broken and the concentration of $Al_2O_3$ increased by adding more aluminum oxide.

Under normal operating conditions the cell is usually fed fresh $Al_2O_3$ at regular intervals, even when no anode effect occurs. In addition, every time the anode effect occurs, as described above, the crust on the cell must be broken and the $Al_2O_3$ concentration increased by adding fresh aluminum oxide, which means that the cells must be serviced. In production therefore, an anode effect is always associated with cell service, which in contrast to normal cell maintenance can be described as "anode effect service".

The aluminum 14 produced, which collects on the carbon floor 15 of the cell, is generally removed once a day from the cell by a special device designed for this purpose.

In the course of time a significant increase in volume of the carbon lining 11 occurs due to penetration of components from the electrolyte. The components meant here are either salts, which are contained in the fluoride melt, or chemical compounds which originate from the melt as a result of reactions which at present are not well understood.

As a result of its increase in volume, the carbon lining presses horizontally against the thermal insulation 13 and the peripheral wall of the steel container 12. The steel is consequently irreversibly deformed, which stresses it beyond its elastic limit and therefore can cause cracking. The carbon lining is deformed too, the carbon lining on the floor usually bowing upwards, with the result that cracks form in its upper surface 15. The liquid aluminum 14 then penetrates these cracks and reacts with the iron cathode bars 17. The damage to the lining of the cell can progress so far that the liquid aluminum is discharged from the cell. The cell then has to be taken out of service and the whole lining replaced before the cell can be put back into service. Such repairs are usually necessary every 2 to 6 years; they are expensive and there is also a loss in production due to the cell being out of service.

Attempts have been made, namely by reinforcing the steel container, to prevent this deformation and cracking. However this cannot be entirely prevented, but only reduced in severity. Furthermore such reinforcement is a significant economical disadvantage, since the cell becomes more expensive and its overall weight is considerably increased.

During the time the cell is not operating it is often necessary to undertake expensive repairs on the steel container in order to eliminate deformation and cracks.

A great deal of effort has been exerted towards eliminating the penetration of electrolyte components into the carbon lining, and with the attendant resultant increase in volume. It has been found, however, that this volume change cannot be entirely prevented and therefore must be accepted as unavoidable.

SUMMARY OF THE INVENTION

The object of the present invention is therefore to provide, for the production of aluminum, an electrolytic cell with a steel container which permits the carbon floor to expand sufficiently so that there is no permanent deformation or cracking of the container, and without there occurring any significant cost increases. In addition, distortion and cracking in the carbon floor are to be reduced.

The object is achieved, by way of the present invention, in that the steel container defines a chamber around the floor to accommodate horizontal expansion of the floor during operation of the cell, the chamber being filled completely with a first material and a second material, the first material being easily compressible, and the second material extending between the floor and the container and being compressible under loads which do not cause any permanent deformation or cracking of the container, but which give rise to reaction forces on the floor which counteract any upward bulging of the floor and any cracking of the upper surface of the floor.

Preferably the chamber is in the form of a recess formed around the container, defined by a projection disposed around a peripheral wall of the container and detachable from the non-deformed container wall.

The separable projection is held in place by conventional methods e.g. using screws or rivets.

The chamber, which serves for accommodating the expanding carbon floor, must not be filled with air, as the oxygen present in the air would oxidize the carbon lining and burn it away. The chamber must therefore be filled in such a way that no air can gather there. The first filler material must easily compressible that it exerts, in a horizontal direction, only a negligibly small reaction force against the expansion in volume of the carbon lining.

A second material, which may be destroyed by the expansion of the floor of the carbon lining, generates a container force, which is exerted below the carbon floor, but above a core zone of the floor of the carbon lining. According to well known rules pertaining to strengths of materials, a core zone is defined as a zone onto which a force is exerted, so as to prevent the generation of any tensile forces. As a result of the counter force exerted by the second material above the core zone, the carbon floor is compressed to such an extent, that both deformations and cracks therein are avoided.

BRIEF DESCRIPTION OF THE DRAWING

The Figures of the accompanying drawings show some embodiments of the invention, by way of example. In these Figures.

DESCRIPTON OF THE PREFERRED EMBODIMENTS

Figure 2:
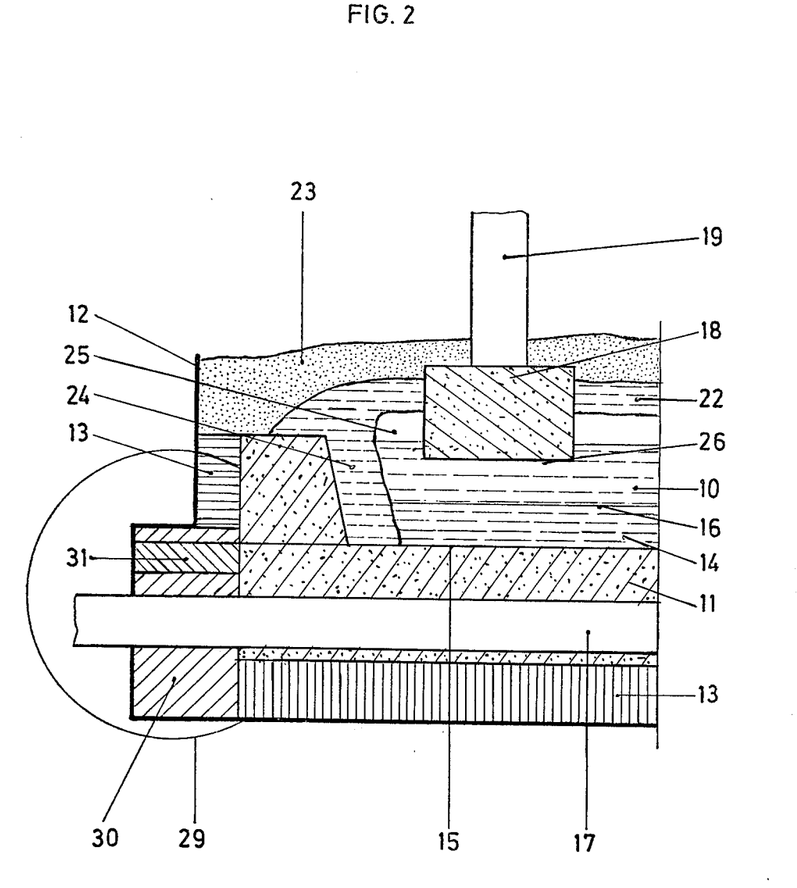
FIG. 2 shows a vertical cross section through part of an electrolytic cell having a projection.

FIG. 2 shows a fluoride melt 10, a carbon lining 11, a steel container 12, a thermal insulation 13, a liquid aluminum 14, an upper surface 15 of the carbon floor, a surface 16 of the liquid aluminum, an iron cathode bar 17, an anode 18, a conductive rod 19, a crust 22 of solidified melt, a layer 23 of aluminum oxide, a lateral ledge 24, and spaces 25 formed above the molten electrolyte.

In accordance with a preferred feature of the invention, the steel container 12 has around the lower part of its peripheral wall a projection which defines a chamber 29, which need not, however, be flush with the container floor, as illustrated. For reasons having to do with ease of manufacture, the type shown in the drawing is preferred, however.

The chamber 29, which extends at least above the upper surface 15 of the carbon floor, is filled with an easily compressible material 30, e.g. with wollastonite, and with a second material 31 which can be crushed only by relatively greater forces. The resultant reaction forces which act on the carbon floor must not be so great that the part of the steel container surrounding the recess 29 becomes permanently deformed. The magnitude of reaction at which the material 31 is crushed must be such that it allows the carbon lining to expand in the horizontal direction without the carbon floor bulging upwards and cracking as is normally the case.

Figure 3:
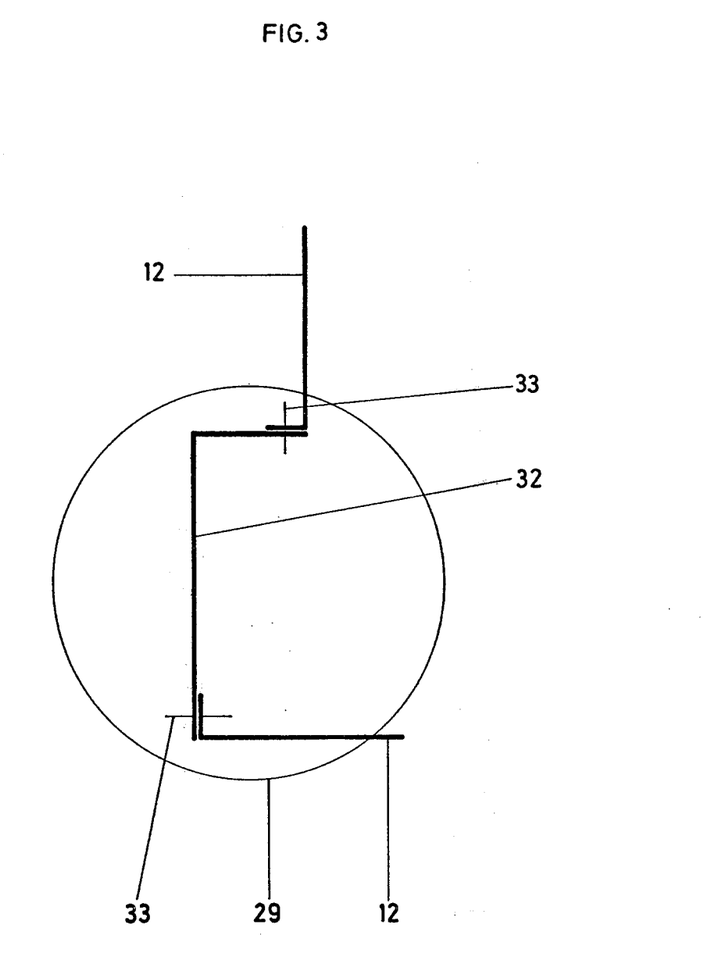
FIG. 3 shows a removable projection on the steel container.

The version shown in FIGS. 3 has the great advantage that repairs to the chamber 29 can be carried out very easily. A removable part 32 is connected to the rest of the steel container, for example by means of connecting devices 33 such as screws or rivets.

As a modification of FIG. 2, the peripheral wall of the steel container 12 may be entirely vertical, in which case the thermal insulation 13 is as wide as the material 30 and 31. However, a projection as in FIG. 2 or FIG. 3 is preferred. It is not essential for the lower boundary of the projection to be flush with the bottom wall of the steel container 12.

Figure 4:
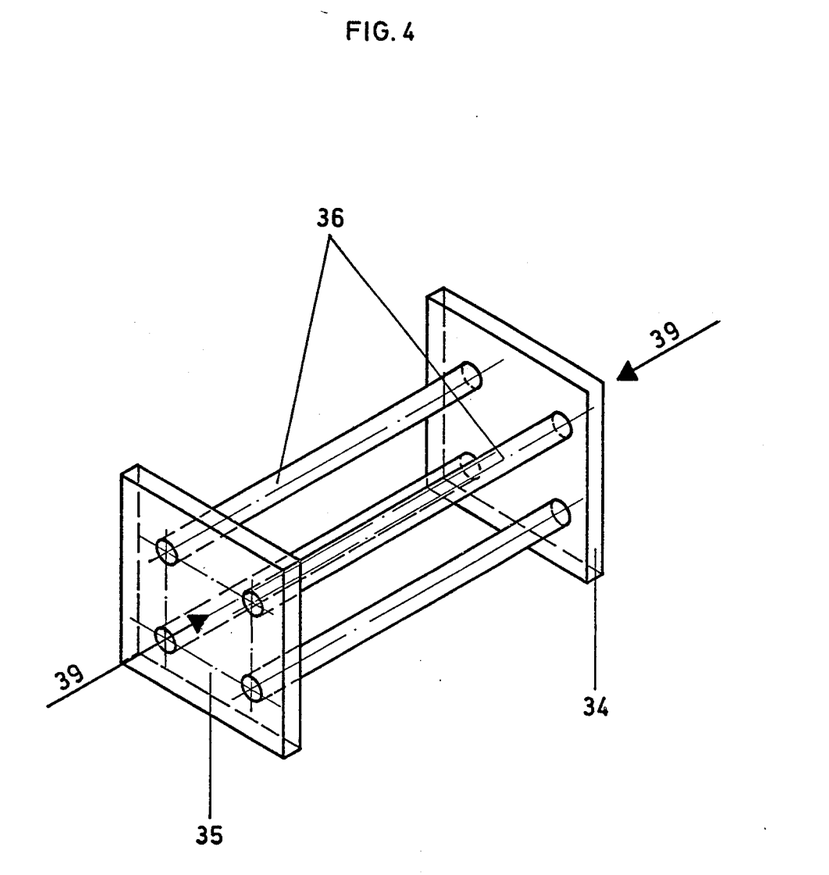
FIGS. 4 to 8 show perspective views of special versions of the second filler material.

FIG. 4 shows a special form of the material 31 for producing the reaction forces. The material is made of devices consisting of two parallel plates 34 and 35, between which are disposed steel rods 36. The plate 35 is laid next to the steel wall 32 of the chamber 29, and the plate 34 is laid next to the carbon lining 11. The steel rods are so dimensioned that they will buckle perpendicularly to the direction 39 under a certain, specific load. The conditions for this load are in general the same as those described for FIG. 2.

Figure 5:
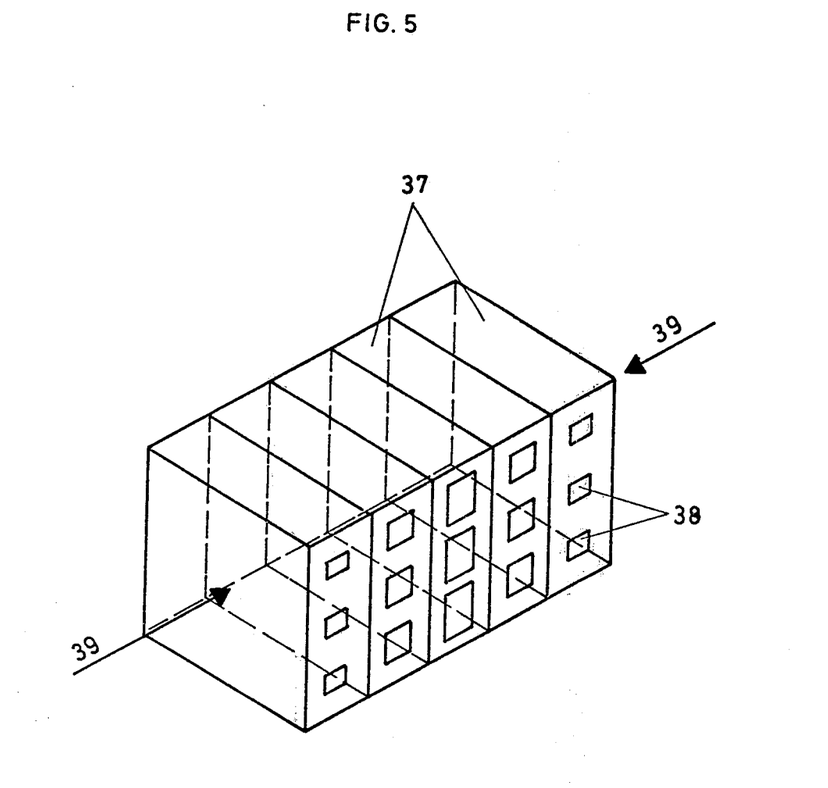

FIG. 5 shows another possible form for the material 31. In this case the material 31 is in the form of an assembly of ceramic bricks 37 which are penetrated by channels 38 formed in a direction transverse to the direction 39 of a force acting on the brick. The cross sectional area of the channels, as viewed in the direction of this force, increases towards the centre of the assembly. This way the assembly is weakened most in the center and therefore the bricks there are crushed together first. The channels 38, which are shown here as being rectangular in cross section, may be of any shape whatsoever, but must be so dimensioned that the bricks 37 at, or after crumbling, produce just that degree of counteracting force as was described for FIG. 2. All the bricks 37 have preferably the same external shape.

Figure 6:
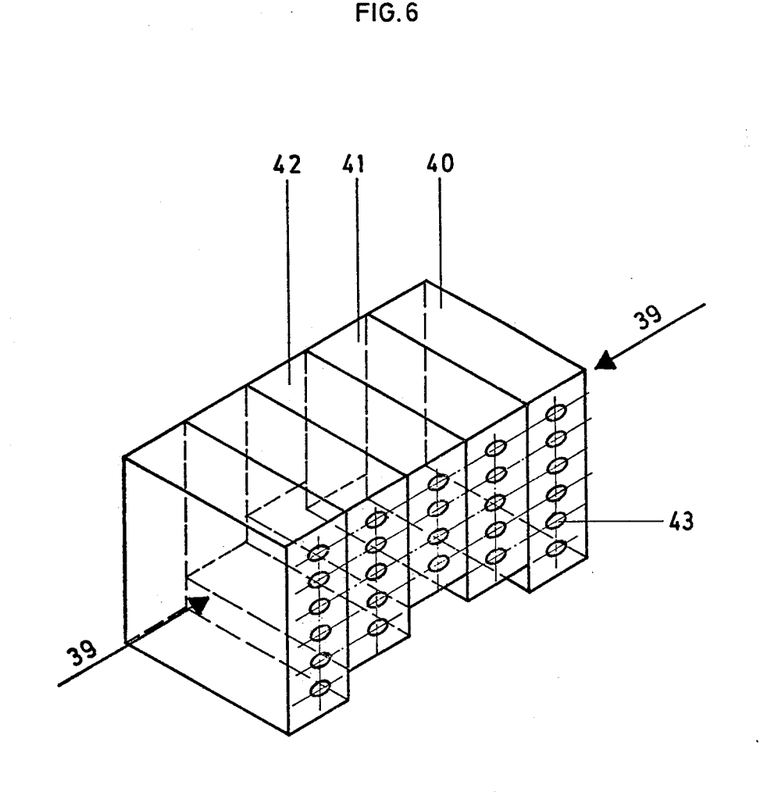

In FIG. 6 the material 31 is made up of bricks 40, 41 and 42 of different sizes, each of which being formed with a channel 43. This results in a relatively smaller reaction force and relatively smaller characteristic forces along a predetermined line. If a sufficiently high force is applied, the brick having the smallest dimension is crushed firstly. As the reaction force due to the expansion of the carbon lining increases further, the next smallest brick is crushed, then a next, and progressively so in the direction of increasing cross section. Compared with the application of bricks of equal size, the bricks shown in FIG. 6 are crushed at a relatively smaller reaction force, which does not rise steeply throughout the crushing process.

Figure 7:
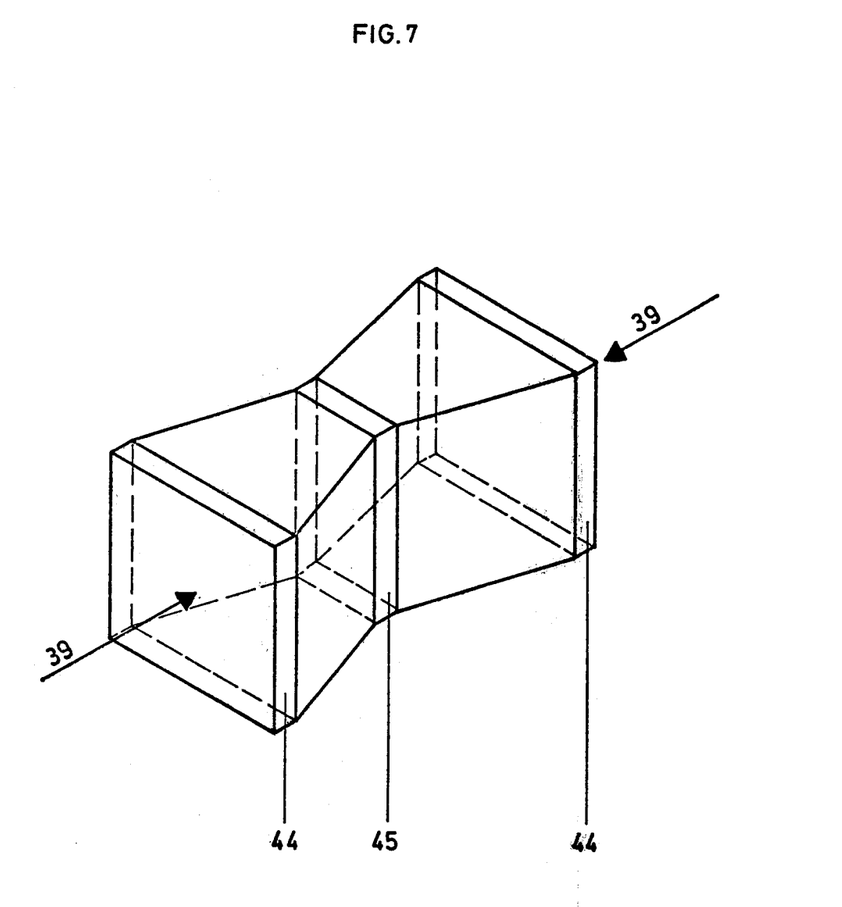

In FIG. 7, as a further variant of the material 31, a ceramic brick is shown having a varying cross section. The cross section decreases from an end having the greatest cross section 44 to the smallest cross section 45, i.e. the material 31 is formed with a constriction. The part of the brick having the smallest cross section is crushed first. If the force exerted increases further, then the crushing progresses in the direction of increasing cross section.

Figure 8:
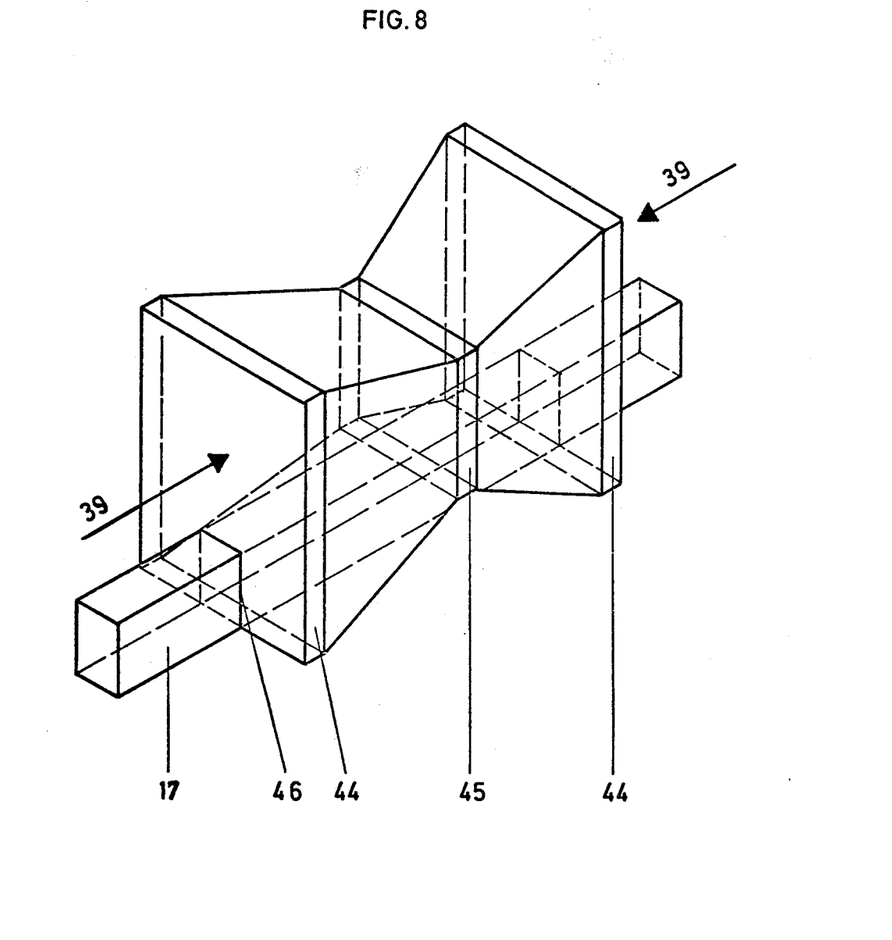

The arrangement of the material 31 and the cathode bar 17 shown and proposed in FIG. 8, can be used in conjunction with all the examples shown in FIGS. 4 to 7. As shown, the ceramic brick of varying cross section (as in FIG. 7) is provided with a recess 46 into which the iron cathode bar fits. The carbon floor, in which the iron cathode bar 17 is embedded, is omitted for reasons of clarity. This version, using a sliding fit of the bricks on the bars, has the advantage that the bars maintain the alignment of the bricks.

In all the examples as represented in FIGS. 4 to 8, the hollow spaces adjoining or shaping the second material, which is only destroyed by greater forces, are filled with an easily compressible material, e.g. with wollastonite.

What we claim is:

1. An electrolytic cell for the production of aluminum,
   comprising in combination:
   a walled metal container defining a chamber,
   a carbon lining disposed within the container, and including a floor having an upper surface, and being normally susceptible to bulging and cracking during operation of the cell, said chamber accommodating the horizontal expansion of the floor of said container during operation of the cell, and
   first and second materials in contact with one another and filling said chamber, the first material extending between said carbon lining and at least one wall of said container and being relatively easily compressible, the second material extending between said carbon lining and at least one wall of said container and being compressible by a load which, while not causing any permanent deformation or cracking of the container, gives rise to a reaction force exerted on the floor of said carbon lining to counteract bulging and cracking of the floor of said carbon lining.

2. An electrolytic cell according to claim 1, wherein said container is formed with an outwardly projecting peripheral bulge defining said chamber.

3. An electrolytic cell according to claim 2, wherein said bulge is releasably connected to said container.

4. An electrolytic cell according to claim 3, further comprising connecting means for connecting said bulge to said container.

5. An electrolytic cell according to claim 1, wherein said first material is wollastonite.

6. An electrolyte cell according to claim 1, wherein the floor of said carbon lining has a central zone, and wherein the reaction force is exerted by the second material below the upper surface of the floor of said carbon lining, but above the central zone of said carbon lining.

7. An electrolytic cell according to claim 1, wherein said second material includes two juxtaposed plates and a plurality of rods extending therebetween for absorbing the load, said rods being adapted to buckle upon application of the load.

8. An electrolytic cell according to claim 1, wherein said second material includes an assembly of ceramic bricks, each of the bricks having at least one longitudinal channel of predetermined cross-section and aligned in a direction at an angle to the direction of the reaction force, the cross-section of the channels of adjoining ones of said ceramic bricks increasing along the direction of the reaction force towards the center of said assembly.

9. An electrolytic cell according to claim 1, wherein said second material includes an assembly of ceramic bricks, each of said bricks having at least one longitudinal channel in a direction at an angle to the direction of the reaction force, the size of adjoining ones of said ceramic bricks decreasing along the direction of the reaction force towards the center of said assembly.

10. An electrolytic cell according to claim 1, wherein said second material includes at least one ceramic brick being tapered along the direction of the reaction force towards the center of said brick.

11. An electrolytic cell according to claim 10, wherein said ceramic brick is formed with a recess, and further comprising a bus bar serving as a cathode fitting into said recess.

* * * * *